(12) United States Patent
Yokota et al.

(10) Patent No.: US 6,312,533 B1
(45) Date of Patent: Nov. 6, 2001

US006312533B1

(54) STAINLESS STEEL MATERIAL WITH EXCELLENT ANTIBACTERIAL PROPERTY AND PROCESS FOR PRODUCING THE SAME

(75) Inventors: Takeshi Yokota, Chiba; Kenji Takao, Chiba; Susumu Satoh, Chiba; Haruhiko Ishizuka, Tokyo; Masaharu Ikeda, Chiba, all of (JP)

(73) Assignee: Kawasaki Steel Corporation, Hyogo (JP)

(*) Notice: Subject to any disclaimer, the term of this patent is extended or adjusted under 35 U.S.C. 154(b) by 0 days.

(21) Appl. No.: 09/720,864

(22) PCT Filed: Apr. 24, 2000

(86) PCT No.: PCT/JP00/02660

§ 371 Date: Jan. 2, 2001

§ 102(e) Date: Jan. 2, 2001

(87) PCT Pub. No.: WO00/66807

PCT Pub. Date: Nov. 9, 2000

(30) Foreign Application Priority Data

Apr. 30, 1999 (JP) .................................................. 11-124731

(51) Int. Cl.[7] .................................................. C23C 28/00
(52) U.S. Cl. .......................... 148/325; 148/273; 148/281; 148/287; 148/276
(58) Field of Search ..................................... 148/273, 276, 148/281, 287, 325; 428/472.1, 472.2

(56) References Cited

U.S. PATENT DOCUMENTS

| | | | | |
|---|---|---|---|---|
| 4,856,174 | * | 8/1989 | Ishizaki et al. | 29/455.1 |
| 5,394,610 | * | 3/1995 | Stoephasius et al. | 29/890 |
| 5,520,664 | * | 5/1996 | Bricault, Jr. et al. | 604/265 |
| 5,681,575 | * | 10/1997 | Burrell et al. | 424/423 |
| 5,695,857 | * | 12/1997 | Burrell et al. | 428/209 |
| 6,102,994 | * | 8/2000 | Zhou et al. | 106/15.05 |
| 6,168,869 | * | 1/2001 | Tomioka et al. | 428/472.2 |
| 6,180,162 | * | 1/2001 | Shigeru et al. | 427/11 |

* cited by examiner

*Primary Examiner*—Roy King
*Assistant Examiner*—Harry D. Wilkins, III
(74) *Attorney, Agent, or Firm*—Young & Thompson

(57) ABSTRACT

The present invention provides a BA-finished stainless steel product having superior antibacterial properties and corrosion resistance and a method for producing the same. Specifically, after a stainless steel product is subjected to BA treatment, the stainless steel product is immersed in a solution containing Ag ions having a concentration of 0.0001 to 1.0 mol/l so that a BA film contains, in area percentage, 0.0002 to 0.05% of Ag particles and Ag compounds, and further, stainless steel product contains 0.001 to 0.10% by weight of Ag and optionally further contains 0.001 to 0.30% by weight of V.

16 Claims, No Drawings

STAINLESS STEEL MATERIAL WITH EXCELLENT ANTIBACTERIAL PROPERTY AND PROCESS FOR PRODUCING THE SAME

TECHNICAL FIELD

The present invention relates to stainless steel products, and more particularly, relates to bright annealing (BA) finished stainless steel products having superior antibacterial properties suitable for use in domestic utensils, medical devices, building materials, etc. Examples of the stainless steel products in the present invention include steel sheets, steel strips, steel pipes, steel wires, and end products made of stainless steels which are BA finished.

BACKGROUND ART

It has been known from old days that silver and copper inhibit pathogenic bacteria, such as Escherichia coli and salmonellae, from proliferating.

Recently, materials to which the bacterial proliferation-inhibiting activity (hereinafter referred to as "antibacterial properties") is imparted using such metals have been developed. For example, Japanese Unexamined Patent Application Publication No. 8-49085 discloses a stainless steel sheet having superior antibacterial properties in which a metal layer or an alloy layer of Cr, Ti, Ni, Fe, etc., containing Ag and/or Cu is formed on the surface of a stainless steel base by magnet sputtering. In the steel sheet, it is preferable that the alloy layer or the metal layer containing 19 to 60% by weight of Ag be formed.

Japanese Unexamined Patent Application Publication No. 8-156175 also discloses a coated steel sheet which can inhibit bacteria from proliferating, in which a pigment containing silver is applied.

However, with respect to the method for forming the alloy layer or the metal layer containing the antibacterial metal on the surface of the steel sheet or to the method for applying the pigment containing the antibacterial metal to the surface of the steel sheet described above, the layer containing the antibacterial metal may be separated or removed by drawing or grinding of the surface, thus canceling the effects thereof, which is disadvantageous. Additionally, when used for kitchen utensils, etc., since surfaces are scrubbed by cleaning, it is not possible to maintain antibacterial properties for a long period of time, which is also disadvantageous.

Japanese Unexamined Patent Application Publication No. 8-239726 discloses a material with antibacterial properties and marine life resistance, which contains 10 to 80% by weight of iron, 1 to 10% by weight of aluminum, and preferably, further contains 1 to 15% by weight of at least one metal selected from the group consisting of chromium, nickel, manganese, and silver, the balance being copper and incidental impurities. However, since the above material is a copper-based alloy or iron-based alloy containing 1 to 10% of aluminum, the workability is decreased, and in particular, it gives rise to a problem when used for tableware, kitchen utensils, electric components, etc., in which the material is formed into sheets.

In view of the problems described above, Japanese Unexamined Patent Application Publication No. 8-104953 discloses an austenitic stainless steel with increased antibacterial properties, containing 1.1 to 3.5% by weight of Cu, Japanese Unexamined Patent Application Publication No. 10-259457 discloses an austenitic stainless steel with increased antibacterial properties, containing 0.5 to 4.0% by weight of Cu and 0.05 to 1.0% by weight of Ag, Japanese Unexamined Patent Application Publication No. 8-104952 discloses a martensitic stainless steel with increased antibacterial properties, containing 0.3 to 5.0% by weight of Cu, and Japanese Unexamined Patent Application Publication No. 9-170053 discloses a ferritic stainless steel with increased antibacterial properties, containing 0.4 to 3.0% by weight of Cu.

However, in order to display antibacterial properties, Cu, as ions, must be dissolved out of the surface of the steel sheet. The dissolution of Cu, as ions, means that a passivation film is destroyed at the spot, and even though antibacterial properties are improved, corrosion resistance is significantly deteriorated. Therefore, in the stainless steel to which a large amount of Cu is added, it is difficult to simultaneously acquire antibacterial properties and corrosion resistance.

Japanese Unexamined Patent Application Publication No. 10-259456 discloses an antibacterial stainless steel sheet containing at least 8% by weight of Cr and 0.05 to 1.0% by weight of Ag, in which the Ag phase having a minor axis of 10 $\mu$m or less is dispersed in the matrix at an areal rate of 0.03% or more.

However, in the technique described in Japanese Unexamined Patent Application Publication No. 10-259456, it is substantially difficult to restrict the minor axis of the Ag phase to 10 $\mu$m or less, and in order to set the areal rate of the Ag phase having the minor axis of 10 $\mu$m or less at 0.03% or more, a large amount of Ag must be added, resulting in a decrease in workability and corrosion resistance, and also a degradation in surface properties.

Although a stainless steel product is generally worked into an end product after being subjected to the descaling process by acid pickling, in the case of a BA-finished stainless steel product, after cold rolling is performed, annealing (bright annealing treatment, i.e., BA treatment) is performed in a reducing atmosphere, and the BA-finished stainless steel product is handled as an end product without being subjected to the descaling process by acid pickling.

In the BA treatment (reduction annealing), an oxide film, which is referred to as a BA film, is generated at a thickness of approximately 0.001 to 0.1 $\mu$m on the surface of the stainless steel product. Antibacterial elements, such as Cu and Ag, in the surface layer of the steel product are not migrated into the BA film by the BA treatment alone, and also, if the surface of the steel product is covered by the BA film, antibacterial elements are not allowed to be dissolved as ions, which may result in a significant decrease in antibacterial properties in the surface portion. Additionally, since the annealing temperature is high in the BA treatment, the antibacterial elements may disappear from the surface layer and a region having a low antibacterial element concentration may be formed in the surface layer, resulting in a decrease in antibacterial properties in the surface portion.

It is an object of the present invention to provide a stainless steel product having superior antibacterial properties and corrosion resistance and a method for producing the same in which the problems associated with the conventional techniques described above are advantageously solved and the antibacterial properties in the surface portion of the end product are enhanced with a relatively low Ag content.

DISCLOSURE OF INVENTION

The present inventors have made every effort to carry out researches to simultaneously obtain antibacterial properties and corrosion resistance in stainless steel products. As a result, it has been found that it is possible to significantly improve the antibacterial properties of a BA-finished stainless steel product without deteriorating corrosion resistance by incorporating Ag or Ag compounds within a proper range into the BA film of the stainless steel product. Furthermore, it has been also found that the antibacterial properties of the BA-finished stainless steel product can be significantly improved by incorporating a slight amount of Ag into the stainless steel product.

The present invention has been achieved based on the knowledge described above.

That is, in one aspect of the present invention, a bright annealing finished stainless steel product having superior antibacterial properties, which is subjected to bright annealing treatment (BA treatment), preferably contains 0.001 to 0.10% by weight of Ag, or further contains 0.001 to 0.30% by weight of V. An oxide film (BA film) formed on the surface by the bright annealing treatment (BA treatment) contains, in area percentage, 0.0002 to 0.05% of Ag particles and Ag compounds (Ag oxides, Ag sulfide, etc.).

In another aspect of the present invention, a method for producing a bright annealing finished stainless steel product having superior antibacterial properties includes the step of immersing the stainless steel product in a solution containing Ag ions with a concentration of 0.0001 to 1.0 mol/liter after the stainless steel product is subjected to bright annealing treatment (BA treatment), so that an oxide film (BA film) formed on the surface of the stainless steel product by the bright annealing treatment (BA treatment) contains, in area percentage, 0.0002 to 0.05% of Ag particles and Ag compounds. In the present invention, preferably, the stainless steel product contains 0.001 to 0.10% by weight of Ag, or further contains 0.001 to 0.30% by weight of V. In the present invention, preferably, the solution is an aqueous solution, and more preferably, the aqueous solution is one of an acid solution and an alkaline solution. In the present invention, the acid solution is preferably a nitric acid solution with a concentration of 0.1 to 60% by weight, and in t he present invention, the alkaline solution is preferably an alkaline solution with a pH of 8.0 or more.

BEST MODE FOR CARRYING OUT THE INVENTION

Any one of a ferritic stainless steel, an austenitic stainless steel, and a martensitic stainless steel which is BA-finished is preferably used for a BA-finished stainless steel product of the present invention.

With respect to the chemical composition, the ferritic stainless steel preferably contains 0.0001 to 0.1% by weight of C, 1.0% by weight or less of Si, 2.0% by weight or less of Mn, 0.1% by weight or less of P, 0.10% by weight or less of S, 8 to 50% by weight of Cr, 0.1% by weight or less of N, and the balance being Fe and incidental impurities. Additionally, the ferritic stainless steel may contain at least one of 0.3% by weight or less of Al, 1.0% by weight or less of Ni, 5.0% by weight or less of Mo, 1.0% by weight or less of Ti, 1.0% by weight or less of Nb, 1.0% by weight or less of Zr, 1.0% by weight or less of Cu, 0.3% by weight of less of W, 0.001 to 0.5% by weight of Co, and 0.01% by weight or less of B.

The austenitic stainless steel preferably contains 0.001 to 0.1% by weight of C, 2.0% by weight or less of Si, 2.0% by weight or less of Mn, 0.1% by weight or less of P, 0.1% by weight or less of S, 10 to 35% by weight of Cr, 6 to 15% by weight of Ni, 0.001 to 0.1% by weight of N, and the balance being Fe and incidental impurities. Additionally, the austenitic stainless steel may contain at least one of 0.3% by weight or less of Al, 3.0% by weight or less of Mo, 1.0% by weight or less of Ti, 1.0% by weight or less of Nb, 1.0% by weight or less of Zr, 1.0% by weight or less of Cu, 0.3% by weight of less of W, 0.001 to 0.5% by weight of Co, and 0.01% by weight or less of B.

The martensitic stainless steel preferably contains 0.001 to 1.0% by weight of C, 1.0% by weight or less of Si, 2.0% by weight or less of Mn, 0.1% by weight or less of P, 0.1% by weight or less of S, 8 to 19% by weight of Cr, 0.001 to 0.1% by weight of N, and the balance being Fe and incidental impurities. Additionally, the martensitic stainless steel may contain at least one of 1.5% by weight or less of Al, 3.0% by weight or less of Ni, 3.0% by weight or less of Mo, 1.0% by weight or less of Ti, 1.0% by weight or less of Nb, 1.0% by weight or less of Zr, 1.0% by weight or less of Cu, 0.3% by weight of less of W, 0.001 to 0.5% by weight of Co, and 0.01% by weight or less of B.

A steel product of the present invention is a stainless steel product subjected to BA treatment, which preferably has the chemical composition in the ranges described above, and a BA film formed on the surface by the BA treatment contains, in area percentage, 0.0002 to 0.05% of Ag particles and Ag compounds. Also, the BA-finished stainless steel product of the present invention preferably has the chemical composition in the ranges described above, and further contains 0.001 to 0.10% by weight of Ag, and more preferably, further contains 0.001 to 0.30% by weight of V.

First, the reasons for specifying the limits in the Ag and V contents in the composition of the stainless steel product of the present invention will be described. Additionally, in the present invention, the compositions other than Ag and V are preferably set within the ranges described above with respect to the various types of known stainless steels.

Ag: 0.001 to 0.10% by weight

A slight amount of Ag contained in the stainless steel product is the bearer of antibacterial properties in the present invention. In order to display stable antibacterial properties, in the present invention, Ag is homogeneously dispersed in the steel product and the existence form thereof is controlled so as to be dissolved at an appropriate rate. That is, the important points are the Ag content for displaying antibacterial properties, the control of the existence form, the addition of a special element for homogeneously dispersing Ag, the control of the production conditions, and so on.

Ag is the most important element in the present invention and is the element which inhibits bacteria from proliferating and increases antibacterial properties. Such effects can be achieved by the addition of 0.001% by weight or more of Ag. However, if more than 0.10% by weight of Ag is added, although antibacterial properties are increased, corrosion resistance is deteriorated, surface defects increase during hot rolling, and a large amount of expensive Ag is added, resulting in an increase in cost, which is economically disadvantageous.

Therefore, the content of Ag in the steel product is limited in the range of 0.001 to 0.10% by weight, and more preferably, 0.01 to 0.05% by weight.

Ag contained in the steel product exists in the forms of Ag particles, Ag oxides, and Ag sulfide. In accordance with the knowledge of the present inventors, Ag oxides have a superior antibacterial action than that of Ag particles, and Ag particles have a superior antibacterial action than that of Ag sulfide. In view of improving antibacterial properties, Ag is preferably present as Ag particles or as Ag particles together with Ag oxides.

V: 0.001 to 0.30% by weight

In addition to Ag in the range described above, V is preferably incorporated in the range of 0.001 to 0.30% by weight. V significantly alleviates the tendency of Ag particles and Ag compounds, such as Ag oxides and Ag sulfide, to be localized in the center of thickness, and homogeneously disperses the Ag particles and Ag compounds in the steel product, and thus being an effective element in improving the antibacterial properties of the steel product. By incorporating 0.001% by weight of more of V, homogeneous antibacterial properties in the surface of the steel product can be achieved. On the other hand, if more than 0.30% by weight of V is incorporated, the workability of the steel product tends to be decreased. Therefore, the V content is preferably limited in the range of 0.001 to 0.30% by weight, more preferably, 0.001 to 0.10% by weight, and further more preferably, 0.010 to 0.025% by weight.

The stainless steel product of the present invention having the composition described above is subjected to BA treatment and a BA film is formed on the surface thereof.

In accordance with the present invention, the BA film contains, in area percentage, 0.0002 to 0.05% of Ag particles and Ag compounds.

When the surface of the steel product is covered by the BA film due to the BA treatment, antibacterial properties of the surface tend to be decreased in comparison with those inside the steel product. Therefore, in the present invention, Ag particles and Ag compounds are incorporated in the BA film in the surface. If the content of the Ag particles and Ag compounds in the BA film is less than 0.0002%, in area percentage, antibacterial properties are less displayed in comparison with the inside of the steel product. On the other hand, if the content of the Ag particles and Ag compounds, in area percentage, exceeds 0.05%, in area percentage, many defects occur in the BA film, thus decreasing the corrosion resistance. Therefore, the content of the Ag particles and Ag compounds in the BA film is limited in the range of 0.0002 to 0.05%, in area percentage, and preferably, 0.001 to 0.03%, in area percentage, and more preferably, 0.001 to 0.02%, in area percentage.

In the present invention, with respect to the steel product which has been subjected to BA treatment, an analysis is carried out to identify the constituents from the surface layer in the depth direction (thickness direction) using a field-emission-type Auger electron spectroscope, a glow-discharge emission spectroscopic analyzer, or the like, and the region from the surface to the level in which the intensities of iron (Fe) and oxygen (O) reach constant values (steady state) is defined as the BA film. Also, in the present invention, with respect to the content of the Ag particles and Ag compounds in the BA film, the surface of the BA film is measured using a field-emission-type Auger electron spectroscope or an electron microanalyzer, and the value of area percentage obtained by an image analyzer is used.

Next, a method for producing a BA-finished stainless steel product in the present invention will be described.

Since the stainless steel product of the present invention can be melted by any known melting method, it is not necessary to particularly limit the melting method.

A molten stainless steel containing preferably 0.001 to 0.10% by weight of Ag, or further containing 0.001 to 0.30% by weight of V is produced by a known melting method.

Although the molten steel produced may be formed into a steel material by a known casting method, in view of productivity and quality, a continuous casting process is preferably employed.

In the continuous casting process, in order to homogeneously disperse Ag particles or Ag compounds in the steel, the casting rate is preferably set in the range of 0.8 to 1.6 m/min. If the casting rate is less than 0.8 m/min, the Ag compounds are coarsened and corrosion resistance is deteriorated. On the other hand, if the casting rate exceeds 1.6 m/min, it is difficult to perform stable casting, and the dispersion of the Ag compounds becomes inhomogeneous. Therefore, the casting rate in the continuous casting process is preferably set in the range of 0.8 to 1.6 m/min.

In the present invention, after the molten stainless steel having the chemical composition described above is formed into a steel material, preferably, under the conditions described above, by continuous casting, the steel material is heated at a predetermined temperature as required, and then a desired hot rolled sheet (steel strip or steel sheet after hot rolling) is produced by hot rolling. The hot rolled sheet is annealed as required, preferably, at a temperature of 700 to 1,200° C., is subjected to acid pickling, followed by cold rolling, and thus a cold rolled sheet (steel strip or steel sheet after cold rolling) having a predetermined thickness is produced.

Preferably, the cold rolled sheet is then subjected to bright annealing (BA) treatment at 700 to 1,200° C. in a reducing atmosphere to produce a BA-finished steel product. By the BA treatment, a BA film is formed on the surface of the steel product.

The BA-finished steel product provided with the BA film is immersed in a solution having an Ag ion concentration of 0.0001 to 1.0 mol/l after the BA treatment is performed or after the product is worked into an end product.

By immersing the steel product into the solution containing Ag ions, the Ag ions in the solution are precipitated in thin portions of the BA film or in defective portions of the BA film, thus greatly improving antibacterial properties of the surface portion. Such improvement of antibacterial properties are displayed at an Ag ion concentration of 0.0001 mol/liter or more in the solution, and tends to saturate at approximately 1.0 mol/liter. If the Ag ion concentration exceeds 1.0 mol/liter, a large amount of an Ag ion former (e.g., Ag particles) must be added into the solution, resulting in an increase in cost. Therefore, the Ag ion concentration in the solution is preferably set in the range of 0.0001 to 1.0 mol/liter, and more preferably, in the range of 0.001 to 0.10 mol/liter.

The Ag ion former to be added in order to incorporate Ag ions into the solution is not particularly limited, and examples thereof are Ag particles, $Ag_2O$ particles, and a silver nitrate solution.

As the solution containing Ag ions into which the steel product provided with the BA film is immersed, any one of solutions (e.g., neutral industrial water, an acid solution, and an alkaline solution) and organic solvents (e.g., acetone) may be preferably used. By immersing the steel product provided with the BA film in the solution containing Ag ions, antibacterial properties can be enhanced. Additionally, the solution is preferably an aqueous solution, and more preferably, one of an acid solution and an alkaline solution.

By using the acid solution or the alkaline solution, adhesion of Ag ions to the BA film is accelerated. Although the reason for this is not clarified yet, it is assumed that precipitates in the BA film which are soluble in an acid or an alkali are dissolved in the solution and the Ag ions adhere to the dissolved portions. Consequently, by immersing the steel product provided with the BA film into the acid solution or the alkaline solution, corrosion resistance is also improved further more in addition to improvement of antibacterial properties.

As the acid solution, a nitric acid solution is preferably used with a concentration of 0.1 to 60% by weight. If the concentration of nitric acid is less than 0.1% by weight, improvement of antibacterial properties is decreased, and if it exceeds 60% by weight, surface luster of the steel product is deteriorated. Therefore, the concentration of the nitric acid solution is preferably set in the range of 0.1 to 60% by weight, more preferably, in the range of 1 to 20% by weight, and further more preferably, in the range of 7 to 13% by weight.

As the alkaline solution, preferably, an alkaline solution with a pH of 8.0 or more is used, more preferably, with a pH of 9.0 or more, and further more preferably, with a pH of 10 or more. In the case of the alkaline solution, in addition to improvement of antibacterial properties, the effect of cleaning the surface is also expected. If the pH is less than 8.0, adhesion of Ag ions is decreased and improvement of antibacterial properties is decreased. Additionally, as the alkaline solution, for example, a NaOH solution may be used.

The immersion time of the BA-finished steel product in the solution is preferably set at 0.1 sec or more. If the immersion time is less than 0.1 sec, adhesion of Ag ions to the BA film is insufficient and antibacterial properties are not improved. On the other hand, if the immersion time exceeds 20 sec, productivity may be decreased or surface luster may be deteriorated, which are disadvantageous. Additionally, the preferable immersion time is 2 sec or more.

In the present invention, although the method for enhancing the antibacterial properties of the surface layer is described with respect to the BA-finished stainless steel product, the method of the present invention is also suitable for a stainless steel sheet which is treated with surface finish other than the BA finish. When antibacterial properties of the surface layer of the stainless steel sheet which is treated with surface finish other than the BA finish are deteriorated for some reason, the antibacterial properties are recovered by immersion into the solution containing Ag ions of the present invention.

EXAMPLES

Stainless steels having chemical compositions shown in Table 1 (austenitic and martensitic) and Table 2 (ferritic) were melted and formed into slabs by continuous casting with various casting rates. Each slab was heated and formed into a hot rolled sheet having a thickness of 4.0 mm by hot rolling. Next, the hot rolled sheet was annealed at 700 to 1,200° C. and subjected to acid pickling, followed by cold rolling to produce a cold rolled sheet having a thickness of 0.8 mm.

The resulting cold rolled sheets were subjected to BA treatment in a reducing atmosphere (a mixed gas of $H_2$ and $N_2$ with a $H_2$ partial pressure of 0.75 atm, dew point −30 to −60° C.) to produce BA-finished steel strips. After the BA treatment, the steel strips were immersed in solutions containing Ag ions having concentrations shown in Table 3 (austenitic and martensitic) and Table 4 (ferritic) for the period of immersion time shown in Table 3 and Table 4. Additionally, the annealing time for the cold rolled sheet was set at 800 to 1,050° C. for ferritic stainless steels, at 900 to 1,200° C. for austenitic stainless steels, and at 780 to 850° C. for martensitic stainless steels. Furthermore, some of the BA-finished steel strips were subjected to press working to form cylinders having a bottom radius of 50 mm and a height of 100 mm. After the press working, the pressed products were also immersed in solutions containing Ag ions having concentrations shown in Table 5 for the period of immersion time shown in Table 5, and a specimen (50 mm×50 mm) for testing antibacterial properties was sampled from the center of the bottom face of each pressed product.

With respect to specimens sampled from the BA-finished stainless steel sheets and BA-finished products, antibacterial testing and corrosion resistance testing were carried out. In order to check the continuity and durability of antibacterial properties, antibacterial testing was also carried out after immersion in boiling water of 100° C. for 24 hours. Additionally, in order to determine the content of Ag and Ag compounds in the BA film, the area percentage was measured by an image analyzer using an electron microanalyzer.

Methods for the individual tests will be briefly described below.

(1) Antibacterial Test

Antibacterial properties were evaluated in accordance with the film contact method employed by Society of Industrial Technology for Antimicrobial Articles.

1) A specimen (50 mm ×50 mm) is cleaned and degreased using absorbent cotton containing 99.5% ethanol or the like.

2) Escherichia coli is dispersed in a 1/500 NB solution. (The number of microorganisms was adjusted to $2.0×10^5$ to $1.0×10^6$ cfu/ml. The 1/500 NB solution corresponds to a normal-broth medium (NB) which is diluted with sterile purified water 500 times. The normal broth medium (NB) comprises 5.0 g of meat extract, 5.0 g of sodium chloride, 10.0 g of peptone, and 1,000 ml of purified water and has a pH of 7.0±0.2.)

3) The bacterial culture is inoculated into specimens (3 pieces each) at a rate of 0.4 ml/25 $cm^2$.

4) The surface of each specimen is covered by a polyethylene film.

5) The specimen is stored for 24 hours at a temperature of 35° C.±1.0° C. and at a RH of 90% or more. (Herein, RH refers to relative humidity.)

6) The number of live microorganisms was measured by agar cultivation (35±1.0° C., 40 to 48 hours). Antibacterial properties were evaluated based on the reduction of microorganisms (an average of 3 pieces) defined by the equation below.

Reduction of microorganisms (%)=(reference number of microorganisms —number of microorganisms after testing)/ (reference number of microorganisms)×100

The reference number of microorganisms is the number of live microorganisms, obtained by antibacterial testing, of the stainless steel which is not subjected to antimicrobial treatment. The number of microorganisms after testing is the number of live microorganisms measured.

(2) Corrosion Resistance Test

Corrosion resistance was evaluated by a salt-drying and wetting combined cycle test.

Two specimens for each steel product were subjected to several cycles (5 to 30 cycles) of treatment set for each steel type, and the rusting area percentage (%) in the surface of the specimen was measured using a CCD camera and an image processing device, where treatments 1) and 2) below were combined as one cycle. The number of cycles repeated was set at 10 cycles for ferritic stainless steels, at 30 cycles for austenitic stainless steels, and at 5 cycles for martensitic stainless steels.

1) After a 5.0% NaCl solution (temperature: 35° C.) is sprayed for 0.5 hour, the specimen is maintained for 1.0 hour in a dry atmosphere at a humidity of 40% or less and at a temperature of 60° C.

2) The specimen is maintained for 1.0 hour in a wet atmosphere at a humidity of 95% or more and at a temperature of 40° C.

The results of the tests are shown in Tables 3, 4, and 5.

In examples of the present invention, antibacterial properties are displayed, as products as well as after immersion in boiling water of 100° C. for 24 hours. Furthermore, it is also apparent that superior antibacterial properties are retained after the products are ground 2 $\mu$m. The examples of the present invention also have superior corrosion resistance with low rusting area percentage. The results described above can be confirmed regardless of types of stainless steels.

In contrast, in comparative examples which are out of the ranges of the present invention, either antibacterial properties are deteriorated or corrosion resistance is deteriorated.

With respect to Steel Product Nos. 16, 29, and 46 in which the Ag content in the steel product is below the preferable lower limit of the present invention, antibacterial properties after grinding are deteriorated. With respect to Steel Nos. 15, 28, 38, and 47 in which the content of Ag particles and Ag compounds in the BA film is below the lower limit of the present invention, although antibacterial properties as products are deteriorated, antibacterial properties are displayed after grinding. On the other hand, with respect to Steel Product Nos. 24 and 53 in which the content of Ag particles and Ag compounds in the BA film is above the upper limit of the present invention, corrosion resistance is deteriorated. In the case in which the method of the present invention is used after BA steel strips are subjected to press working, sufficient antibacterial properties and corrosion resistance are also observed (Steel Product Nos. 54 to 59).

Additionally, with respect to antibacterial properties, the reduction of microorganisms of 99.0% or more is considered to be satisfactory. With respect to corrosion resistance, steel products which meet the reduction of microorganisms of 99.0% or more and which have the rusting area percentage of 15% or less are considered to be satisfactory.

INDUSTRIAL APPLICABILITY

In accordance with the present invention, stainless steel products of any one of ferritic, austenitic, and martensitic types having superior antibacterial properties and corrosion resistance can be provided, which is significantly effective in industrial use. The present invention is also advantageous in that stainless steel products having superior antibacterial properties and corrosion resistance, which are used for members subjected to forming and grinding and in which hygiene is important, for example, those used in wet environments, such as kitchens and bathtubs, in which bacteria easily proliferate, can be easily produced.

TABLE 1

| Steel | | Chemical composition (wt %) | | | | | | | | | | | | | | | | |
|---|---|---|---|---|---|---|---|---|---|---|---|---|---|---|---|---|---|---|
| No. | Type | C | Si | Mn | P | S | Cr | N | Al | Mo | Cu | Ni | Ti | Nb | B | W | Co | Ag | V |
| 11 | Austenitic | 0.05 | 0.31 | 1.05 | 0.03 | 0.006 | 18.2 | 0.04 | 0.002 | 0.04 | 0.30 | 8.30 | — | — | — | — | — | 0.042 | 0.01 |
| 12 | | 0.05 | 0.30 | 1.04 | 0.03 | 0.005 | 18.2 | 0.04 | 0.002 | 0.04 | 0.31 | 8.20 | — | — | — | 0.01 | 0.12 | 0.035 | 0.04 |
| 13 | | 0.05 | 0.29 | 1.05 | 0.03 | 0.006 | 18.5 | 0.04 | 0.001 | 0.04 | 0.30 | 8.30 | — | — | — | — | — | — | — |
| 14 | | 0.04 | 0.33 | 1.03 | 0.03 | 0.005 | 18.2 | 0.04 | 0.002 | 0.04 | 0.31 | 8.30 | — | — | — | — | — | 0.005 | 0.01 |
| 15 | | 0.05 | 0.32 | 1.04 | 0.03 | 0.006 | 18.2 | 0.04 | 0.002 | 0.04 | 0.31 | 8.30 | — | — | — | — | — | 0.10 | 0.25 |
| 16 | | 0.05 | 0.30 | 1.02 | 0.03 | 0.005 | 18.2 | 0.04 | 0.002 | 0.04 | 0.30 | 8.30 | — | — | — | — | — | 0.70 | — |
| 17 | | 0.05 | 0.30 | 1.02 | 0.03 | 0.005 | 18.2 | 0.04 | 0.002 | 0.04 | 0.30 | 8.30 | — | — | — | — | — | 0.055 | 0.11 |
| 18 | | 0.05 | 0.30 | 1.01 | 0.03 | 0.008 | 18.3 | 0.03 | 0.001 | 0.04 | 0.30 | 8.15 | — | — | — | — | — | 0.047 | 0.03 |
| 19 | | 0.04 | 0.30 | 1.00 | 0.03 | 0.005 | 18.2 | 0.03 | 0.001 | 0.03 | 0.29 | 8.05 | — | — | — | — | — | 0.062 | — |
| 21 | Martensitic | 0.04 | 0.30 | 0.29 | 0.02 | 0.006 | 13.0 | 0.009 | 0.010 | — | — | 0.07 | — | — | — | — | — | 0.035 | 0.01 |
| 22 | | 0.04 | 0.31 | 0.29 | 0.02 | 0.005 | 13.0 | 0.009 | 0.010 | — | — | 0.07 | — | — | — | 0.01 | 0.10 | 0.038 | 0.12 |
| 23 | | 0.04 | 0.31 | 0.32 | 0.02 | 0.005 | 13.1 | 0.010 | 0.010 | — | — | 0.06 | — | — | — | — | — | — | — |
| 24 | | 0.33 | 0.34 | 0.44 | 0.02 | 0.006 | 12.6 | 0.025 | 0.002 | — | — | 0.07 | — | — | — | — | — | 0.031 | 0.30 |
| 25 | | 0.31 | 0.33 | 0.40 | 0.02 | 0.005 | 12.2 | 0.010 | 0.001 | — | — | 0.08 | — | — | — | — | — | 0.10 | — |

TABLE 2

| Steel No. | Type | C | Si | Mn | P | S | Cr | N | Al | Mo | Cu | Ni | Ti | Nb | B | W | Co | Ag | V |
|---|---|---|---|---|---|---|---|---|---|---|---|---|---|---|---|---|---|---|---|
| 31 | Ferritic | 0.06 | 0.31 | 0.60 | 0.03 | 0.003 | 16.2 | 0.031 | 0.001 | — | — | 0.20 | — | — | — | — | — | 0.037 | 0.010 |
| 32 | | 0.05 | 0.30 | 0.61 | 0.03 | 0.003 | 16.3 | 0.035 | 0.001 | — | — | 0.31 | — | — | — | 0.01 | 0.11 | 0.041 | 0.012 |
| 33 | | 0.05 | 0.30 | 0.58 | 0.03 | 0.003 | 16.2 | 0.070 | — | — | 0.12 | — | — | — | 0.01 | 0.15 | 0.020 | 0.021 | — |
| 34 | | 0.007 | 0.10 | 0.30 | 0.03 | 0.008 | 16.2 | 0.008 | 0.020 | — | — | 0.11 | 0.16 | — | — | 0.01 | 0.10 | 0.050 | 0.010 |
| 35 | | 0.005 | 0.06 | 0.18 | 0.02 | 0.004 | 17.8 | 0.008 | 0.030 | 1.45 | — | 0.12 | 0.23 | — | — | — | — | — | 0.014 |
| 36 | | 0.004 | 0.07 | 0.19 | 0.03 | 0.005 | 18.1 | 0.009 | 0.020 | 1.38 | — | 0.12 | 0.19 | 0.01 | 0.0011 | 0.01 | 0.11 | 0.035 | 0.013 |
| 37 | | 0.011 | 0.31 | 0.47 | 0.03 | 0.009 | 17.7 | 0.015 | 0.002 | — | — | 0.13 | — | 0.44 | — | 0.01 | 0.10 | 0.028 | 0.010 |
| 38 | | 0.008 | 0.47 | 0.14 | 0.02 | 0.002 | 19.1 | 0.014 | 0.019 | — | 0.55 | 0.38 | — | — | — | — | — | 0.046 | 0.020 |
| 39 | | 0.011 | 0.49 | 0.51 | 0.03 | 0.004 | 11.4 | 0.008 | 0.033 | — | — | 0.11 | 0.16 | — | — | — | — | 0.022 | 0.011 |
| 40 | | 0.06 | 0.30 | 0.61 | 0.02 | 0.003 | 16.1 | 0.041 | 0.002 | — | — | 0.18 | — | — | — | — | — | 0.030 | — |
| 41 | | 0.05 | 0.33 | 0.60 | 0.02 | 0.002 | 16.3 | 0.028 | 0.001 | — | — | 0.21 | — | — | — | — | — | — | 0.015 |
| 42 | | 0.0004 | 0.001 | 0.001 | 0.001 | 0.0003 | 16.2 | 0.0008 | 0.0005 | — | — | — | — | — | — | — | — | 1.10 | 0.012 |
| 43 | | 0.06 | 0.30 | 0.60 | 0.03 | 0.002 | 16.3 | 0.035 | 0.002 | — | — | 0.10 | — | — | — | — | — | 0.035 | 0.009 |
| 44 | | 0.06 | 0.30 | 0.59 | 0.03 | 0.003 | 16.2 | 0.044 | 0.002 | — | — | 0.31 | — | — | — | — | — | 0.008 | 0.037 |
| 45 | | 0.06 | 0.31 | 0.61 | 0.03 | 0.006 | 17.5 | 0.010 | 0.002 | — | — | 0.10 | — | — | — | — | — | 0.10 | 0.037 |
| 46 | | 0.05 | 0.30 | 0.57 | 0.03 | 0.004 | 16.2 | 0.040 | 0.001 | — | — | 0.09 | — | — | — | — | — | 0.07 | — |

TABLE 3

| Steel product No. | Steel No. | Type | Casting rate (m/min) | Surface finish | Ag ion concentration mol/l | Immersion liquid Type | Concentration* wt % | pH | Immersion time sec | Ag content in film Area Percentage % | Antibacterial properties (Reduction of microorganisms) (%) As BA-finished product | After 24 hours at 100° C. | After 2 μm grinding | Corrosion resistance Rusting area percentage (%) | Remarks |
|---|---|---|---|---|---|---|---|---|---|---|---|---|---|---|---|
| 11 | 11 | Austenitic | 1.0 | BA | 0.011 | HNO$_3$ solution | 9 | 0 | 5 | 0.01 | 100 | 100 | 100 | 1 | (a) |
| 12 | 12 | | 1.0 | BA | 0.011 | HNO$_3$ | 20 | 0 | 0.2 | 0.005 | 100 | 100 | 100 | 0 | (a) |
| 13 | | | 1.0 | BA | 0.015 | NaOH | 1 | 13 | 6 | 0.02 | 100 | 100 | 100 | 0 | (a) |
| 14 | | | 0.9 | BA | 0.010 | Industrial | — | — | 4 | 0.01 | 99.4 | 99.2 | 100 | 0 | (a) |
| 15 | | | 1.4 | BA | — | HNO$_3$ | 13 | 0 | 25 | 0.0001 | 92.2 | 91.0 | 99.9 | 2 | (b) |
| 16 | 13 | | 1.1 | BA | 0.010 | HNO$_3$ | 8 | 0 | 7 | 0.01 | 100 | 100 | 5 | 3 | (a) |
| 17 | 14 | | 1.2 | BA | 0.008 | HNO$_3$ | 0.0001 | 9 | 6 | 0.01 | 99.2 | 99.1 | 99.3 | 0 | (a) |
| 18 | | | 1.2 | BA | 0.005 | NaOH | 0.1 | 12 | 6 | 0.005 | 100 | 100 | 99.2 | 0 | (a) |
| 19 | 15 | | 1.2 | BA | 0.012 | HNO$_3$ | 12 | 0 | 8 | 0.01 | 100 | 100 | 100 | 8 | (a) |
| 20 | 16 | | 1.5 | BA | 0.001 | HNO$_3$ | 9 | 0 | 12 | 0.01 | 100 | 100 | 100 | 25 | (a) |
| 21 | 17 | | 1.2 | BA | 0.007 | Industrial | — | — | 7 | 0.01 | 99.7 | 99.5 | 100 | 3 | (a) |
| 22 | 18 | | 1.2 | BA | 0.010 | HNO$_3$ | 11 | 0 | 8 | 0.02 | 100 | 100 | 100 | 2 | (a) |
| 23 | 19 | | 1.2 | BA | 0.027 | HNO$_3$ | 10 | 0 | 9 | 0.03 | 100 | 99.9 | 99.1 | 7 | (a) |
| 24 | | | 1.0 | BA | 0.2 | HNO$_3$ | 9 | 0 | 100 | 0.09 | 100 | 100 | 99.1 | 39 | (b) |
| 25 | 21 | Martensitic | 0.9 | BA | 0.010 | HNO$_3$ | 10 | 0 | 5 | 0.01 | 100 | 100 | 100 | 7 | (a) |
| 26 | 22 | | 0.9 | BA | 0.012 | HNO$_3$ | 10 | 0 | 6 | 0.01 | 100 | 100 | 100 | 5 | (a) |
| 27 | | | 0.9 | BA | 0.012 | NaOH | 0.01 | 11 | 4 | 0.02 | 100 | 100 | 100 | 5 | (a) |
| 28 | | | 1.6 | BA | — | Industrial | — | — | 7 | 0.0001 | 98.3 | 98.2 | 100 | 8 | (b) |
| 29 | 23 | | 1.0 | BA | 0.014 | HNO$_3$ | 9 | 0 | 8 | 0.01 | 100 | 100 | 0 | 8 | (a) |
| 30 | 24 | | 1.0 | BA | 0.008 | HNO$_3$ | 7 | 0 | 5 | 0.01 | 100 | 100 | 100 | 5 | (a) |
| 31 | 25 | | 1.2 | BA | 0.015 | HNO$_3$ | 11 | 0 | 9 | 0.01 | 100 | 99.8 | 99.2 | 11 | (a) |

*) Concentration of HNO$_3$ or NaOH in solution
(a) Example of present invention
(b) Comparative example

TABLE 4

| Steel product No. | Steel No. | Type | Casting rate (m/min) | Surface finish | Immersion liquid Ag ion concentration mol/l | Type | Concentration* wt % | pH | Immersion time sec | Ag content in film Area percentage % | Antibacterial properties (Reduction of microorganisms (%)) As BA-finished product | After 24 hours at 100° C. | After 2 μm grinding | Corrosion Rusting area percentage (%) | Remarks |
|---|---|---|---|---|---|---|---|---|---|---|---|---|---|---|---|
| 32 | 31 | Ferritic | 1.2 | BA | 0.093 | HNO₃ | 0.2 | 2 | 4 | 0.01 | 100 | 100 | 100 | 5 | (a) |
| 33 |    |    | 1.0 | BA | 0.020 | HNO₃ | 10 | 0 | 6 | 0.01 | 100 | 100 | 100 | 5 | (a) |
| 34 | 32 |    | 1.1 | BA | 0.001 | NaOH | 10 | 14 | 5 | 0.01 | 100 | 100 | 100 | 0 | (a) |
| 35 |    |    | 1.1 | BA | 0.012 | NaOH | 1 | 13 | 7 | 0.02 | 100 | 100 | 100 | 0 | (a) |
| 36 |    |    | 1.0 | BA | 0.011 | Industrial | — | — | 0.3 | 0.008 | 99.3 | 99.1 | 100 | 0 | (a) |
| 37 |    |    | 1.5 | BA | 0.009 | NaOH | 0.0001 | 9 | 1 | 0.02 | 100 | 100 | 100 | 7 | (b) |
| 38 |    |    | 0.8 | BA | — | HNO₃ | 10 | 0 | 30 | 0.0001 | 97.5 | 97 | 99.8 | 6 | (a) |
| 39 | 33 |    | 0.9 | BA | 0.008 | Industrial | — | — | 6 | 0.002 | 99.5 | 99.3 | 99.7 | 7 | (a) |
| 40 | 34 |    | 1.3 | BA | 0.012 | HNO₃ | 1 | 1 | 4 | 0.02 | 100 | 100 | 100 | 3 | (a) |
| 41 | 35 |    | 1.5 | BA | 0.015 | HNO₃ | 7 | 0 | 5 | 0.01 | 100 | 100 | 100 | 4 | (a) |
| 42 | 36 |    | 1.5 | BA | 0.007 | HNO₃ | 10 | 0 | 6 | 0.01 | 100 | 100 | 99.9 | 4 | (a) |
| 43 | 37 |    | 1.2 | BA | 0.010 | HNO₃ | 8 | 0 | 7 | 0.01 | 100 | 100 | 100 | 4 | (a) |
| 44 | 38 |    | 1.0 | BA | 0.005 | HNO₃ | 13 | 0 | 7 | 0.01 | 100 | 100 | 99.8 | 10 | (a) |
| 45 | 39 |    | 1.2 | BA | 0.002 | HNO₃ | 11 | 0 | 6 | 0.01 | 100 | 100 | 99.9 | 5 | (a) |
| 46 | 40 |    | 1.1 | BA | 0.011 | HNO₃ | 10 | 0 | 4 | 0.02 | 100 | 99.1 | 2 | 6 | (a) |
| 47 | 41 |    | 0.9 | BA | — | HNO₃ | 10 | 0 | 3 | 0.0001 | 98.1 | 90.2 | 100 | 36 | (b) |
| 48 | 42 |    | 1.0 | BA | 0.006 | HNO₃ | 10 | 0 | 8 | 0.02 | 100 | 100 | 100 | 4 | (a) |
| 49 | 43 |    | 1.1 | BA | 0.025 | HNO₃ | 52 | 0 | 15 | 0.03 | 100 | 100 | 99.1 | 2 | (a) |
| 50 | 44 |    | 1.3 | BA | 0.031 | HNO₃ | 20 | 0 | 20 | 0.03 | 100 | 100 | 100 | 10 | (a) |
| 51 | 45 | 1.5 | BA | 0.010 | HNO₃ |   | 9 | 4 | 0.01 | 100 | 100 | 35 | (a) | (a) |   |
| 52 | 46 |    | 1.2 | BA | 0.027 | HNO₃ | 10 | 9 | 0.03 | 100 | 100 | 99.2 | 8 | (a) |
| 53 |    | 1.2 | BA | 0.5 | HNO₃ |   | 9 | 0 | 120 | 0.10 | 100 | 99.1 | 42 | (b) |   |

*) Concentration of HNO₃ or NaOH in solution
(a) Example of present invention
(b) Comparative example

TABLE 5

| Steel product No. | Steel No. | Type | Casting rate (m/min) | Surface finish | Immersion liquid Ag ion concentration mol/l | Immersion liquid Type | Immersion liquid Concentration* wt % | Immersion liquid pH | Immersion time sec | Ag content in film Area percentage % | Antibacterial properties (Reduction of microorganisms (%)) As pressed product after BA | Antibacterial properties After 24 hours at 100° C. | Antibacterial properties After 2 μm grinding | Corrosion resistance Rusting area percentage (%) | Remarks |
|---|---|---|---|---|---|---|---|---|---|---|---|---|---|---|---|
| 54 | 12 | Austenitic | 1.1 | BA → press | 0.025 | HNO₃ solution | 9 | 0 | 8 | 0.02 | 100 | 100 | 100 | 10 | (a) |
| 55 |   |   | 1.0 | BA → press | 0.015 | NaOH solution | 0.1 | 12 | 6 | 0.02 | 100 | 100 | 100 | 9 | (a) |
| 56 | 22 | Martensitic | 1.0 | BA → press | 0.018 | HNO₃ solution | 10 | 0 | 4 | 0.01 | 99.8 | 99.4 | 100 | 9 | (a) |
| 57 |   |   | 0.9 | BA → press | 0.020 | NaOH solution | 0.01 | 11 | 10 | 0.03 | 100 | 100 | 100 | 7 | (a) |
| 58 | 32 | Ferritic | 0.9 | BA → press | 0.022 | HNO₃ solution | 9 | 0 | 9 | 0.02 | 100 | 99.9 | 100 | 4 | (a) |
| 59 |   |   | 1.1 | BA → press | 0.020 | NaOH solution | 0.1 | 12 | 6 | 0.02 | 100 | 100 | 99.9 | 6 | (a) |

*) Concentration of HNO₃ or NaOH in solution
(a) Example of present invention
(b) Comparative example

What is claimed is:

1. A bright annealing finished stainless steel product having antibacterial properties, which is subjected to bright annealing treatment, containing 8% by weight or more of Cr, wherein an oxide film formed on the surface of the steel product by the bright annealing treatment contains, in area percentage, 0.0002 to 0.05% of Ag particles and Ag compounds.

2. A bright annealing finished stainless steel product having antibacterial properties according to claim 1, wherein the stainless steel product contains 0.001 to 0.10% by weight of Ag.

3. A bright annealing finished stainless steel product having antibacterial properties according to claim 2, wherein the stainless steel product further contains 0.001 to 0.30% by weight of V.

4. A method for producing a bright annealing finished stainless steel product having antibacterial properties comprising the steps of subjecting the stainless steel product to bright annealing treatment and then immersing the stainless steel product in a solution containing Ag ions with a concentration of 0.0001 to 1.0 mol/l so that an oxide film formed on the surface of the stainless steel product by the bright annealing treatment contains, in area percentage, 0.0002 to 0.05% of Ag particles and Ag compounds.

5. A method for producing a bright annealing finished stainless steel product having antibacterial properties according to claim 4, wherein the stainless steel product contains 0.001 to 0.10% by weight of Ag.

6. A method for producing a bright annealing finished stainless steel product having antibacterial properties according to claim 5, wherein the stainless steel product further contains 0.001 to 0.30% by weight of V.

7. A method for producing a bright annealing finished stainless steel product having antibacterial properties according to claim 4, wherein the solution containing Ag ions contains Ag ions having a concentration of 0.001 to 0.10 mol/l.

8. A method for producing a bright annealing finished stainless steel product having antibacterial properties according to claim 7, wherein the solution containing Ag ions is an aqueous solution.

9. A method for producing a bright annealing finished stainless steel product having antibacterial properties according to claim 8, wherein the aqueous solution containing Ag ions is one of an acid solution and an alkaline solution.

10. A method for producing a bright annealing finished stainless steel product having antibacterial properties according to claim 9, wherein the acid solution is a nitric acid solution with a con centration of 0.1 to 60% by weight.

11. A method for producing a bright annealing finished stainless steel product having antibacterial properties according to claim 9, wherein the alkaline solution is an alkaline solution with a pH of 8.0 or more.

12. A method for producing a bright annealing finished stainless steel product having antibacterial properties according to claim 5, wherein the stainless steel product contains 0.01% by weight or more to less than 0.05% by weight of Ag.

13. A method for producing a bright annealing finished stainless steel product having antibacterial properties according to claim 6, wherein the stainless steel product contains 0.001 to 0.10% by weight of V.

14. A method for producing a bright annealing finished stainless steel product having antibacterial properties according to claim 4, wherein an oxide film formed on the surface of the stainless steel product contains, in area percentage, 0.001% by weight or more to less than 0.03% of Ag particles and Ag compounds.

15. A method for producing a bright annealing finished stainless steel product having antibacterial properties according to claim 4, wherein the immersion time in the solution containing Ag ions is 0.1 second or more.

16. A method for producing a bright annealing finished stainless steel product having antibacterial properties according to claim 4, wherein the immersion time in the solution containing Ag ions is in the range of to 20 seconds.

* * * * *